United States Patent
Heyrend et al.

(10) Patent No.: US 6,453,193 B1
(45) Date of Patent: Sep. 17, 2002

(54) APPARATUS AND METHOD FOR DIFFERENTIATING BETWEEN LOW SENSORY ATTENTIONAL DISORDER AND AFFECTIVE DISORDERS

(76) Inventors: F. LaMarr Heyrend, 411 N. Allumbaugh, Boise, ID (US) 83704; Donald R. Bars, 5121 N. Mountain View, Boise, ID (US) 83704

( * ) Notice: Subject to any disclaimer, the term of this patent is extended or adjusted under 35 U.S.C. 154(b) by 0 days.

(21) Appl. No.: 09/808,206

(22) Filed: Mar. 13, 2001

(51) Int. Cl.[7] ............................................... A61B 5/04
(52) U.S. Cl. ................................................... 600/544
(58) Field of Search .................................. 600/544, 545

(56) References Cited

U.S. PATENT DOCUMENTS

| | | |
|---|---|---|
| 4,862,359 A | 8/1989 | Trivedi et al. |
| 4,955,388 A | 9/1990 | Silberstein |
| 5,320,109 A | 6/1994 | Chamoun et al. |
| 5,331,969 A | 7/1994 | Silberstein |
| 5,377,100 A * | 12/1994 | Pope et al. .................... 341/20 |
| 5,447,166 A | 9/1995 | Gevins |
| 5,730,146 A | 3/1998 | Itil et al. |
| 5,891,050 A | 4/1999 | Gansler et al. |
| 5,983,129 A | 11/1999 | Cowan et al. |
| 6,044,292 A | 3/2000 | Heyrend et al. |
| 6,097,980 A * | 8/2000 | Monastra et al. ........... 600/544 |
| 6,115,631 A | 9/2000 | Heyrend et al. |
| 6,167,298 A * | 12/2000 | Levin ......................... 600/545 |

OTHER PUBLICATIONS

Medical Procedure Patents, The 1996 Amendment and Who Is Really Liable, an article by Randall R. Bateman and W. Wayne Western of Thorpe, North & Western, Intellectual Property Today, Dec. 1997 Handbook of Psychophysiology, edited by Norman S. Greenfield, University of Wisconsin and Richard A. Stenbach, University of California at San Diego.

Boise, Idaho 83704 Pattern Reversal Visual Evoked Potentials and Explosive Behaviors, by F. LaMarr Heyrend, Donald R. Bars, C. Dene Simpson, James C. Munger, Zane Nelson and John Burns (corresponding author: Donald R. Bars, Ph.D.

* cited by examiner

*Primary Examiner*—Kevin Shaver
*Assistant Examiner*—Navin Natnithithadha
(74) *Attorney, Agent, or Firm*—Frank J. Dykas; Robert L. Shaver; Stephen M. Nipper

(57) ABSTRACT

An apparatus and method of testing an individual to identify whether the individual is experiencing: (a) solely an attention disorder (ADD) based upon a low sensory arousal system; (b) another disorder (attentive-type); or (c) a combination of low sensory system attention disorder (ADD) and other attentive disorders.

20 Claims, 3 Drawing Sheets

APPARATUS AND METHOD FOR DIFFERENTIATING BETWEEN LOW SENSORY ATTENTIONAL DISORDER AND AFFECTIVE DISORDERS

BACKGROUND OF THE INVENTION

1. Technical Field

This invention generally relates to an apparatus and method for identifying people with attentional disorders based upon a low sensory arousal system by obtaining and processing electroencephalographic information and applying that data to an algorithm to differentiate between low sensory attentional disorders and other, affective type, disorders.

2. Background

In the field of child and adolescent psychiatry, Attention-Deficit/Hyperactivity Disorder, originally known as minimal brain dysfunction, has been theorized to be of a neurobiological nature. The predominant view is that cognitive and behavioral deficits exhibited with this disorder are the consequences of brain dysfunction although the exact etiology and biological substrata such as lowered levels of reticular activating system excitation which results in low cortical arousal, cortical immaturity or delayed maturation and/or attention-inhibition deficits is not known with any degree of certainty.

There are a number of attentional disorders based upon a low sensory arousal system. Perhaps the best known, and most common of these is Attention-Deficit/Hyperactivity Disorder, for which a definition is found in the American Psychiatric Association Diagnostic and Statistical Manual of Mental Disorders. It states: "[t]he essential feature of Attention-Deficit/Hyperactivity Disorder is a persistent pattern of inattention and/or hyperactivity-impulsivity that is more frequent and severe than is typically observed in individuals at a comparable level of development. . . . There must be clear evidence of interference with developmentally appropriate social, academic, or occupational functioning. . . . The disturbance does not occur exclusively during the course of a Pervasive Developmental Disorder, Schizophrenia, or other Psychotic Disorder and is not better accounted for by another mental disorder (e.g. a Mood Disorder, Anxiety Disorder, Dissociative Disorder, or Personality Disorder. . . . " Attention-Deficit/Hyperactivity Disorder is also found in those suffering from other Attentive Disorders such as obsessive compulsive disorders, bi-polar disorders, rumination disorders, manic and hypo-manic disorders, and depression.

Some disorders, such as rumination in conjunction with obsessive/compulsive and manic disorders are often misdiagnosed as strictly Attention-Deficit/Hyperactivity Disorder. When misdiagnosed as Attention-Deficit/ Hyperactivity Disorder, individuals may be erroneously prescribed stimulant medications. Stimulant medications for those suffering from obsessive/compulsive, bi-polar and manic disorders is not appropriate, and results in the individual becoming extremely tired and will increase the aggressive, agitated rebound effect in the evenings when the stimulants wear off. When a hypo-manic suffering from rumination is misdiagnosed as Attention-Deficit/Hyperactivity Disorder and given stimulant medication, the patient is put at risk psychiatrically and educationally. In effect, it is the misdiagnosis and incorrectly prescribed stimulant which may exacerbate psychotic symptoms or actually induce psychosis. In academic environments, such as children at school, such individuals may be more behaviorally compliant, and still suffer decreased cognitive retention, leading to diminished learning potential. In such cases, parents and teachers will typically know that the stimulation medication is not perfect, but is still better than nothing. However, when properly diagnosed, individuals, particularly children suffering from obsessive-compulsive, bi-polar or manic disorders exhibiting ruminating behavior, can be treated effectively.

Accordingly, it is an object of the present invention to provide an apparatus and method for identifying whether a person is experiencing: solely an attention disorder based upon a low sensory arousal system; other, attentive type, disorders; or a combination of low sensory system attention disorder and other attentive disorders, and thus to more accurately segregate and appropriately treat these individuals.

DISCLOSURE OF INVENTION

These objects are achieved using a testing apparatus which includes an EEG Data Acquisition and Analysis System, which is electrically interconnected to a head assembly containing a plurality of EEG electrodes. The output from the EEG Data Acquisition and Analysis System is sent to a microprocessor where two primary functions of the testing system are performed. These are, the quantification of a standard EEG into absolute powers in the delta, theta, alpha and beta frequency bands and the timing, synchronization and averaging of a series of displays of a paradigm generating a visually evoked response.

Also electrically interconnected to the microprocessor is a visual display device for periodically displaying a plurality of sequential, visual paradigms to a test subject. Hard copy output devices, such as a printer and/or a video output are also interconnected to the microprocessor.

In use, the testing system is used to identify the type of attention disorder an individual is afflicted with. The individual to be tested is first seated comfortably in a chair and sixteen (16) electrodes are attached to the scalp of the individual to be tested in accordance with the International 10–20 System of the American Electroencephalographic Society's guidelines, namely to locations F7, F3, F4, F8, T3, C3, CZ, C4, T4, T5, P3, PZ, P4, T6, 01 and 02. Electrode impedance is maintained at less than 2.0 kilo-ohms and the impedance between homologous sites maintained within 1.0 kilo-ohms. The gain for the EEG Data Acquisition and Analysis System is set at 30,000, with a low pass filter at 100 Hz, and a high pass filter at 1.0 Hz, and a 60 Hz notch filter is set in.

A standard quantitative electroencephalogram is then performed, at which time the EEG Data Acquisition and Analysis System, working in conjunction with the microprocessor, provides a measurement as to the absolute power of the electroencephalograph in the delta, theta, alpha and beta frequency bands, all in the absence of any visual or auditory stimulus.

Next, a visually evoked potential test is conducted using a visual checkerboard pattern reversal and a flash paradigm displayed on the visual device at eye level, 76 cm in front of the individual being tested. The pattern is reversed every 0.59 seconds for a total of 1.7 stimuli per second. A 256 and a 512 millisecond (ms) epoch is utilized with a five millisecond pre-stimulus time. The intensity of the background stimulus is 12.69 candelas per square meter, and the flash is 19.26 candelas per square meter. The test subject is instructed to visually fixate on a red dot centered on the visual device, is requested not to speak, and to remain relaxed with as little movement as possible throughout the two minutes of recording time.

The visually evoked response to each display of a paradigm, as recorded by the EEG Data Acquisition and Analysis System, is then recorded in the microprocessor in a synchronized manner with the time of the display of the paradigm and then averaged together to cancel out the potentials of brain activities that are not related to the visually evoked response, thus generating, in microvolts, the potential of the visually evoked response over a period of time from immediately prior to the display of the paradigm to the time of approximately 500 milliseconds after cessation of the displayed paradigm.

Next, the theta-to-beta ratio, as taken at the electrode placement location CZ is computed. Then the maximum positive voltage potential, in microvolts, of the visually evoked response at a time of approximately 100 milliseconds after cessation of the displayed visual checkerboard paradigm as averaged as previously described is measured at the O1 and O2 electrode sites, said maximum measurement is hereinafter defined as the P100MAX value. And finally, the maximum positive voltage potential, in microvolts, of the visually evoked flash response at a time of approximately 200 milliseconds after cessation of the displayed visual paradigms, is measured at the F3 and F4 electrode sites, said maximum measurement is hereinafter defined as the P200MAX value.

An algorithm is then applied to this data. If the theta-to-beta ratio is equal to, or greater than four, indicating an excess of slow wave activity, the person tested is identified as having a low sensory attentional disorder. If the theta-to-beta ratio is less than four then the person tested is identified as having some other, attentive type, disorder.

Next, in the case of the person identified as having an existing low sensory attentional disorder, if the maximum positive voltage potential of the P100MAX wave is less than 10.0 microvolts ($\mu$V), and the maximum positive voltage potential of the P200MAX wave is less than 6.0 $\mu$V, the person may be identified as having only a low sensory attentional disorder. If either the P100MAX is 10 $\mu$V or greater, or P200MAX is 6 $\mu$V or greater, the person tested is identified as having a low sensory attentional disorder and at least one other affective disorder. The other specific affective disorder, or disorders, may then be identified based upon comorbid affective components using other diagnostic techniques known in the prior art.

In the case of the person identified as not having an existing low sensory attentional disorder, if the maximum positive voltage potential of the P100MAX wave is less than 10.0 $\mu$V, and the positive voltage potential of the P200MAX wave is less than 6 $\mu$V, the person may be identified as having only one affective disorder, probably depression. If either the P100MAX is 10 $\mu$V or greater, or P200MAX is 6 $\mu$V or greater, the person tested is identified as suffering from at least one other affective disorder and possibly more. Again known prior art diagnostic techniques may be used to evaluate the comorbid affective components exhibited by the person tested.

BEST MODE FOR CARRYING OUT INVENTION

What follows is a description of an apparatus and method of testing an individual to identify whether the individual is experiencing: (a) solely an attention disorder based upon a low sensory arousal system; (b) another disorder (attentive-type); or (c) a combination of low sensory system attention disorder and other attentive disorders.

Figure 1:
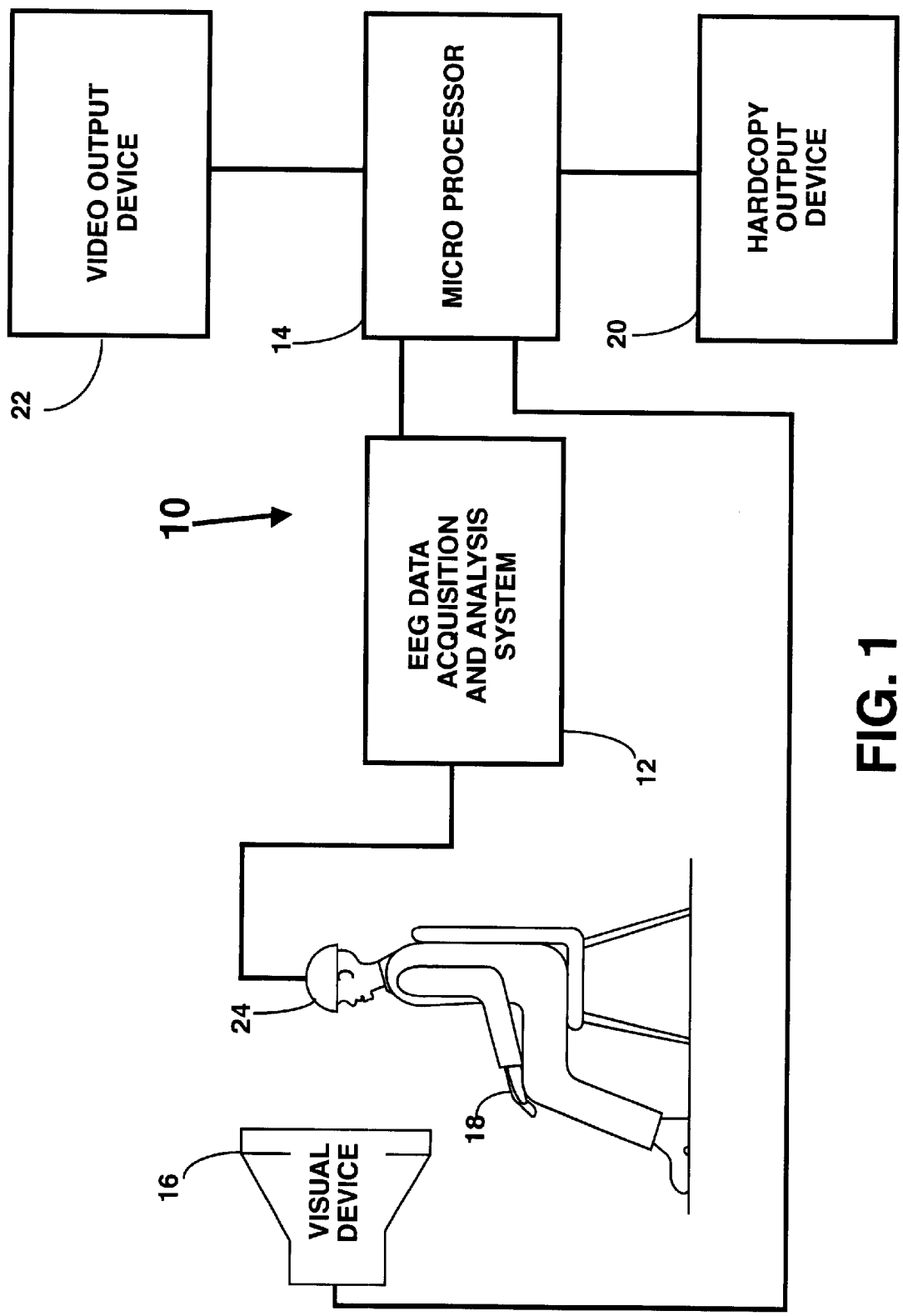
FIG. 1 is a representational schematic of the testing apparatus.

Referring initially to FIG. 1, there is shown in representational schematic format the apparatus, or testing system 10. At the heart of testing system 10 is the EEG Data Acquisition and Analysis System 12, which is electrically interconnected to a head assembly 24 containing a plurality of EEG electrodes. The EEG Data Acquisition and Analysis System 12 output is sent to at least one microprocessor 14 where two primary functions of the testing system 10 are performed.

Also electrically interconnected to microprocessor 14 are visual device 16. Visual device 16 is used to periodically display a plurality of sequential visual paradigms to a test subject 18.

The two functions performed in microprocessor 14 are the quantification of a standard EEG into absolute powers in delta, theta, alpha and beta frequency bands, and the second function being the timing, synchronization and averaging of visually evoked responses to a periodic display of a paradigm using visual device 16. Averaging is used to average out random waves and thus quantify the actual visual evoked response over a period of time relative to each of the sequential paradigm displays.

A hard copy output device 20 is also provided, typically is a standard printer capable of printing tables of data and accurate graphic displays. Optionally, a video output device 22, typically a standard high resolution video display screen, may be provided for real time displays of the same data.

Figure 2:
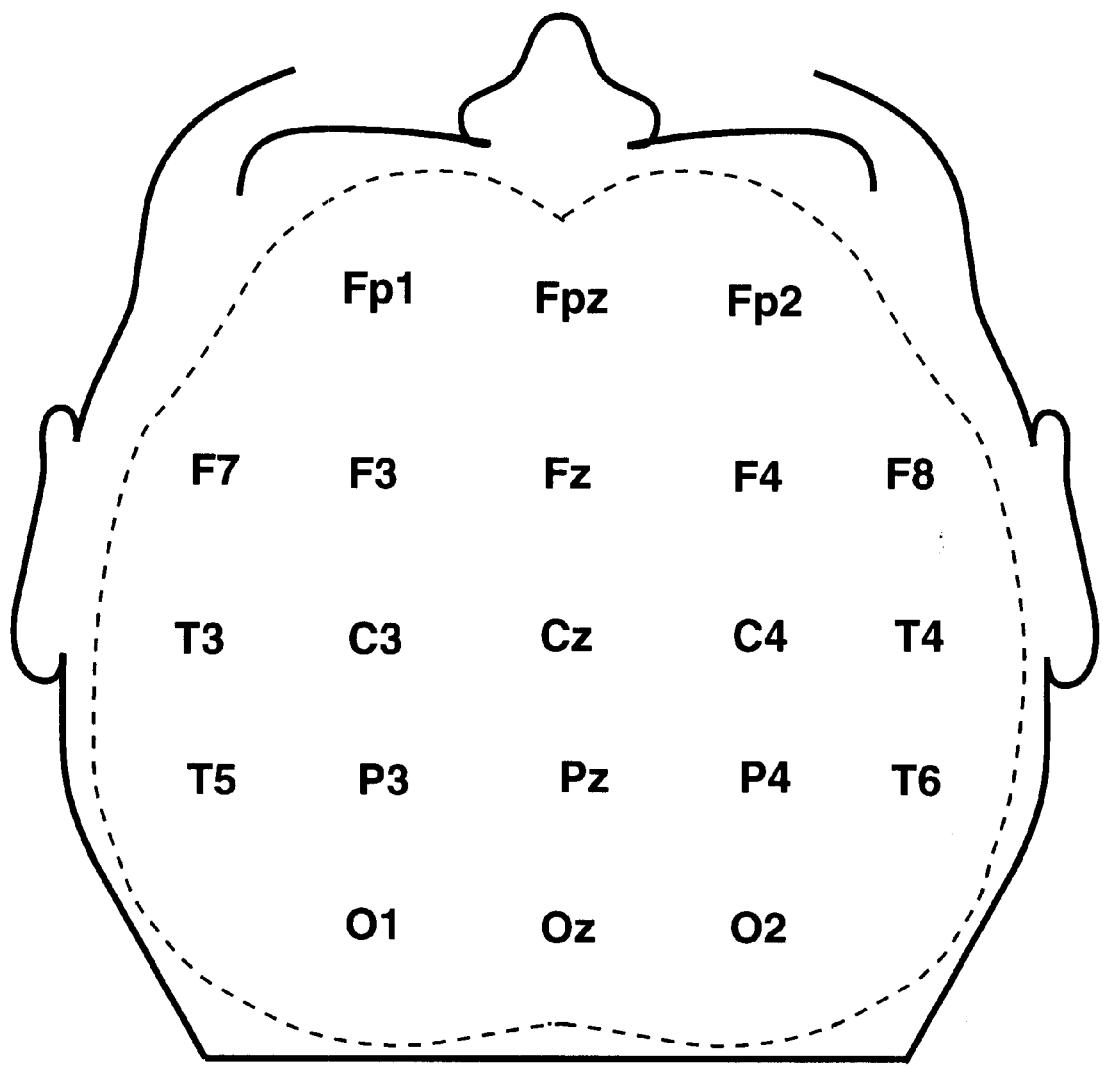
FIG. 2 is a representational map of the scalp of a person showing the location and designator for standard electrodes at standard sites in accordance with the American Electroencephalographic Society's Electrode Placement International 10–20 Standard System for measuring a person's brain waves.

To use system 10 to identify the particular disorder effecting an individual, the individual 18 to be tested is first seated comfortably in a chair and sixteen electrodes contained within head assembly 24 are attached to the scalp of the individual 18 in accordance with the International 10–20 System of the American Electroencephalographic Society's guidelines, namely to the individual's scalp at locations F7, F3, F4, F8, T3, C3, CZ, C4, T4, T5, P3, PZ, P4, T6, O1 and O2, as shown in FIG. 2. Electrode impedance is maintained at less than 2.0 Kohms and the impedance between homologous sites maintained within 1.0 Kohms. The gain for EEG Data Acquisition and Analysis System 12 is set at 30,000, with a low pass filter at 100 Hz, and the high pass filter at 1.0 Hz, and a 60 Hz notch filter is set in.

A standard quantitative electroencephalogram is then performed, at which time EEG Data Acquisition and Analysis System 12, working in conjunction with microprocessor 14, provides a measurement as to the absolute power of the electroencephalograph, in delta, theta, alpha and beta frequency bands, all in the absence of any visual or auditory stimulus. This may all be accomplished in accordance with the teachings of U.S. Pat. Nos. 4,862,359, 6,044,292, and 6,115,631.

Figure 3:
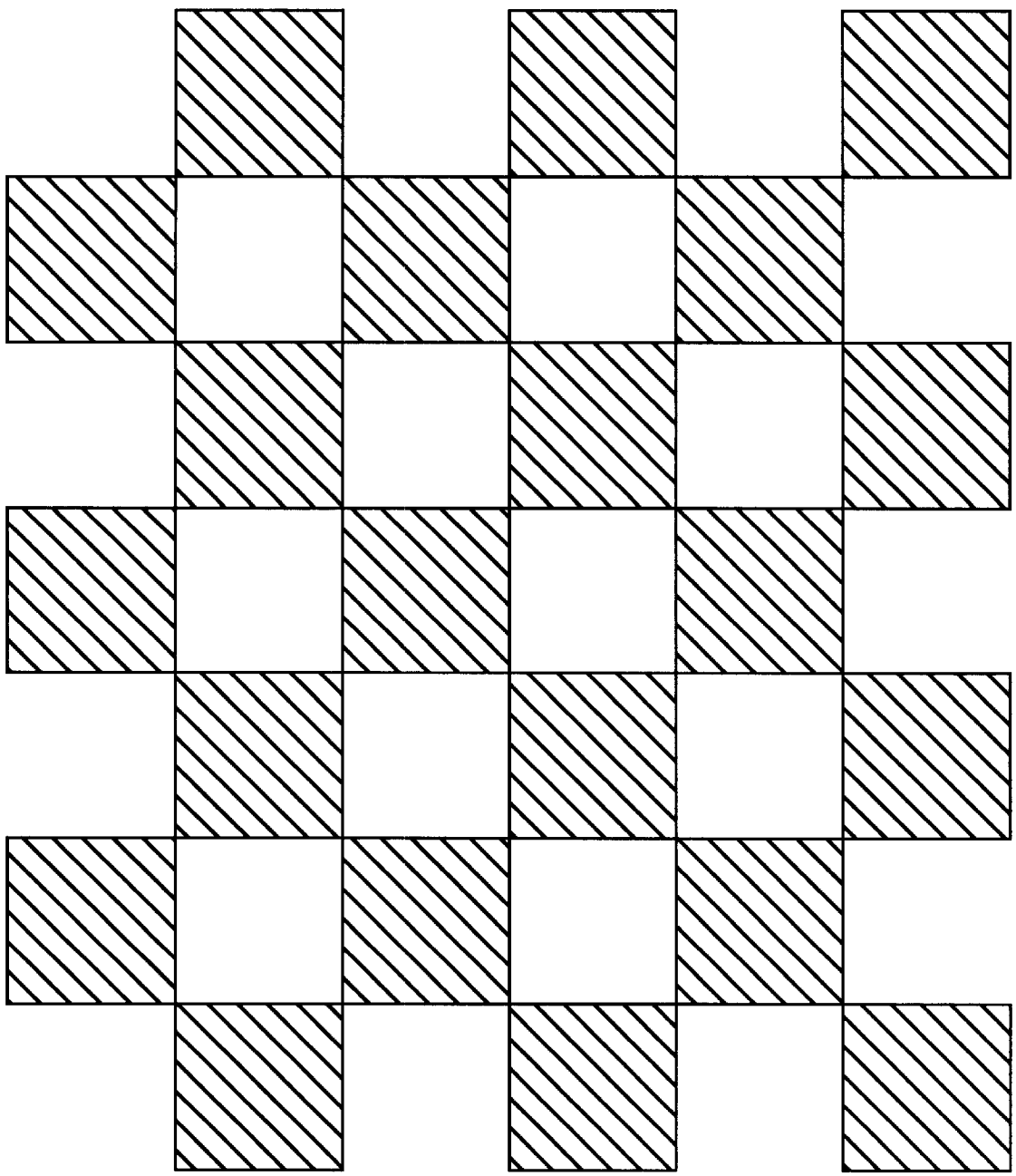
FIG. 3 is a representational drawing of a checkerboard pattern/reversal paradigm used in the present invention to generate visually evoked potentials in the brain.

Next, in the preferred embodiment, a visually evoked potential test is conducted using checkerboard pattern reversal and a flash visual evoked paradigm displayed on visual device 16 at eye level, and 76 cm in front of test subject individual 18. The paradigm is flashed every 0.59 seconds for a total of 1.7 stimuli per second. Although a variety of visual paradigms may be used, the preferred visual paradigm is shown in FIG. 3. A 256 and a 512 millisecond (ms) epoch is utilized with a 5 ms pre-stimulus time. The intensity of the background stimulus is 12.69 candelas per square meter ($cd/m^2$), and the flash is 19.26 $cd/M^2$. The test subject 18 is instructed to visually fixate on a red dot centered on visual device 16, is requested not to speak, and to remain relaxed with as little movement as possible throughout the two minutes of recording time.

The visually evoked response to each display of a paradigm, as recorded by EEG Data Acquisition and Analysis System 12, is then recorded in microprocessor 14 in a synchronized manner with the time of the display of the paradigm, and then averaged together, to cancel out the potentials of brain activities that are not related to the visually evoked response, thus generating, in microvolts ($\mu V$), the potential of the visually evoked response over a period of time from immediately prior to the display of the paradigm to the time of approximately 500 ms after cessation of the displayed paradigm.

Next, in the preferred embodiment of the present invention, three data measurements are taken. First, the theta-to-beta (T/B) ratio, as taken at the electrode placement location CZ, as shown in FIG. 2, is computed.

Second, the maximum positive voltage potential, in microvolts ($\mu V$), of the visually evoked response at a time of approximately 100 milliseconds (ms) after cessation of the displayed visual paradigms as averaged as previously described is measured at the O1 and O2 electrode sites, said measurement is hereinafter defined as the P100MAX value.

Third, the maximum positive voltage potential, in microvolts ($\mu V$), of the visual evoked response at a time of approximately 200 milliseconds after cessation of the displayed visual paradigms, is measured at the F3 and F4 electrode sites, said measurement is hereinafter defined as the P200MAX value.

While this disclosure lists particular suitable electrode sites, other sites may work also.

This data (the T/B ratio, the P100MAX value, and the P200MAX value) is then analyzed to identify whether the individual is experiencing: (a) solely an attention disorder based upon a low sensory arousal system; (b) another disorder (attentive-type); or (c) a combination of low sensory system attention disorder and other attentive disorders.

If the T/B ratio is equal to or greater than four, indicating an excess of slow wave activity, the person tested is identified as having a low sensory attentional disorder.

If the T/B ratio is less than four then the person tested may be identified as having some other, attentive type, disorder.

For individuals identified as having an existing low sensory attentional disorder, if the maximum positive voltage potential of the P100MAX wave is less than 10 $\mu V$, and the maximum positive voltage potential of the P200MAX wave is less than 6 $\mu V$, the person may be identified as having only a low sensory attentional disorder.

For individuals identified as having an existing low sensory attentional disorder, if either the P100MAX is 10 $\mu V$ or greater, or P200MAX is 6 $\mu V$ or greater, the person tested is identified as having a low sensory attentional disorder and at least one other affective disorder(s). The other affective disorder(s), may then be identified based upon comorbid affective components using other diagnostic techniques known in the prior art.

In the case of the person identified as not having an existing low sensory attentional disorder, if the maximum positive voltage potential of the P100MAX wave is less than 10 $\mu V$, and the positive voltage potential of the P200MAX wave is less than 6 $\mu V$, the person may be identified as having only one affective disorder, probably depression.

In the case of the person identified as not having an existing low sensory attentional disorder, if either the P100MAX is 10 $\mu V$ or greater, or P200MAX is 6 $\mu V$ or greater, the person tested is identified as suffering from at least one other affective disorder or possibly more. Again known prior art diagnostic techniques may be used to evaluate the comorbid affective components exhibited by the person tested.

While there is shown and described the present preferred embodiment of the invention, it is to be distinctly understood that this invention is not limited thereto but may be variously embodied to practice within the scope of the following claims.

We claim:

1. A method of identifying the low sensory input system attentional disorder(s) of a person, said method for use with an EEG Data Acquisition and Analysis System which is electrically interconnected to a head assembly containing a plurality of EEG electrodes for sensing brain waves, wherein said method further utilizes a device operable to display a series of paradigms of a pre-selected design, illumination, and frequency, said paradigms evoking brain wave responses sensed by said EEG electrodes and sent to a microprocessor for synchronizing the recording and averaging, said method comprising the steps of:

attaching said electrodes to the scalp of said person at predetermined electrode placement locations for measuring said person's brain waves;

positioning said person to view said paradigms;

displaying to said person sequentially displayed paradigms;

measuring the maximum amplitude of theta activity at a first electrode placement location during a plurality of points in time after termination of each of the displays of said paradigms, averaging said theta activity measurements to determine a theta number;

measuring the maximum amplitude of beta activity at said first electrode placement location during a plurality of points in time after termination of each of the displays of said paradigms, averaging said beta activity measurements to determine a beta number;

determining a theta-to-beta ratio by dividing said theta number by said beta number;

simultaneously measuring a first maximum positive voltage potential at a second electrode placement location and at a third electrode placement location during a plurality of predetermined points in time after termination of each of the displays of said paradigms, averaging said first maximum positive voltage potential measurements to determine a P100MAX number; and, simultaneously measuring a second maximum positive voltage potential at a fourth electrode placement location and at a fifth electrode placement location during a plurality of predetermined points in time after termination of each of the displays of said paradigms, averaging said second maximum positive voltage potential measurements to determine a P200MAX number.

2. The method of claim 1 further comprising the steps of:
identifying the person as having a low sensory attentional disorder if said theta-to-beta ratio is greater than or equal to 4; and
identifying the person as having a some other, attentive type, disorder if said theta-to-beta ratio is less than 4.

3. The method of claim 1 further comprising the step of identifying the person as having a low sensory attentional disorder and at least one other affective disorder if said theta-to-beta ratio is greater than or equal to 4 and said P100Max number (measured in microvolts) is greater than or equal to 10.0 microvolts.

4. The method of claim 1 further comprising the step of identifying the person as having a low sensory attentional disorder and at least one other affective disorder if said theta-to-beta ratio is greater than or equal to 4 and said P200Max number (measured in microvolts) is greater than or equal to 6.0 microvolts.

5. The method of claim 1 further comprising the step of identifying the person as having only one affective disorder if said theta-to-beta ratio is less than 4 and said P100Max number (measured in microvolts) is less than 10.0 microvolts.

6. The method of claim 1 further comprising the step of identifying the person as having only one affective disorder if said theta-to-beta ratio is less than 4 and said P200Max number (measured in microvolts) is less than 6.0 microvolts.

7. The method of claim 1 further comprising the step of identifying the person as having at least one other affective disorder if said theta-to-beta ratio is less than 4 and said P100Max number (measured in microvolts) is greater than or equal to 10.0 microvolts.

8. The method of claim 1 further comprising the step of identifying the person as having at least one other affective disorder if said theta-to-beta ratio is less than 4 and said P200Max number (measured in microvolts) is greater than or equal to 6.0 microvolts.

9. The method of claim 1 wherein electrode placement is made in accordance with the American Electroencephalographic Society's Electrode Placement International 10–20 Standard System, wherein said Standard System defines locations CZ, O1, O2, F3, and F4, and wherein said first electrode placement location is at CZ, wherein said second electrode placement location is at O1, wherein said third electrode placement location is at O2; wherein said fourth electrode placement location is at F3; and wherein said fifth electrode placement location is at F4.

10. The method of claim 1 wherein said maximum amplitude of theta activity is measured immediately after the termination of each of the displays of said paradigms and wherein said maximum amplitude of beta activity is measured immediately after the termination of each of the displays of said paradigms.

11. The method of claim 1 wherein the measurement of the first maximum positive voltage potential at the second and third electrode placement locations takes place approximately 100 milliseconds after termination of each of the displays of said paradigms.

12. The method of claim 1 wherein the measurement of the second first maximum positive voltage potential at the fourth and fifth electrode placement locations takes place approximately 200 milliseconds after termination of each of the displays of said paradigms.

13. A method of identifying the low sensory input system attentional disorders) of a person, said method for use with an EEG Data Acquisition and Analysis System which is electrically interconnected to a head assembly containing a plurality of EEG electrodes for sensing brain waves, wherein said method further utilizes a device operable to display a series of paradigms of a pre-selected design, illumination, and frequency, said paradigms evoking brain wave responses sensed by said EEG electrodes and sent to a microprocessor for synchronizing the recording and averaging, said method comprising the steps of:

attaching said electrodes to the scalp of said person at predetermined electrode placement locations for measuring said person's brain waves;

positioning said per son to view said paradigms;

displaying to said person sequentially displayed paradigms;

measuring the maximum amplitude of theta activity at a first electrode placement location during a plurality of points in time after termination of each of the displays of said paradigms, averaging said theta activity measurements to determine a theta number;

measuring the maximum amplitude of beta activity at said first electrode placement location during a plurality of points in time after termination of each of the displays of said paradigms, averaging said beta activity measurements to determine a beta number;

determining a theta-to-beta ratio by dividing said theta number by said beta number;

wherein said maximum amplitude of theta activity is measured immediately after the termination of each of the displays of said paradigms; and wherein said maximum amplitude of beta activity is measured immediately after the termination of each of the displays of said paradigms.

14. The method of claim 13 further comprising the steps of:

identifying the person as having a low sensory attentional disorder if said theta-to-beta ratio is greater than or equal to 4; and identifying the person as having a some other, attentive type, disorder if said theta-to-beta ratio is less than 4.

15. The method of claim 13 comprising the additional steps of:

simultaneously measuring a first maximum positive voltage potential at a second electrode placement location and at a third electrode placement location during a plurality of predetermined points in time after termination of each of the displays of said paradigms, averaging said first maximum positive voltage potential measurements to determine a P100MAX number;

simultaneously measuring a second maximum positive voltage potential at a fourth electrode placement location and at a fifth electrode placement location during a plurality of predetermined points in time after termination of each of the displays of said paradigms, averaging said second maximum positive voltage potential measurements to determine a P200MAX number;

wherein the measurement of the first maximum positive voltage potential at the second and third electrode placement locations takes place approximately 100 milliseconds after termination of each of the displays of said paradigms; and wherein the measurement of the second first maximum positive voltage potential at the fourth and fifth electrode placement locations takes place approximately 200 milliseconds after termination of each of the displays of said paradigms.

16. The method of claim 15 further comprising the step of identifying the person as having a low sensory attentional disorder and at least one other affective disorder if said theta-to-beta ratio is greater than or equal to 4 and said P100Max number (measured in microvolts) is greater than or equal to 10.0 microvolts.

17. The method of claim 15 further comprising the step of identifying the person as having a low sensory attentional disorder and at least one other affective disorder if said theta-to-beta ratio is greater than or equal to 4 and said P200Max number (measured in microvolts) is greater than or equal to 6.0 microvolts.

18. The method of claim 13 further comprising the steps of:

identifying the person as having only one affective disorder if said theta-to-beta ratio is less than 4 and said P100Max number (measured in microvolts) is less than 10.0 microvolts; and identifying the person as having only one affective disorder if said theta-to-beta ratio is less than 4 and said P200Max number (measured in microvolts) is less than 6.0 microvolts.

19. The method of claim 15 further comprising the steps of:

identifying the person as having at least one other affective disorder if said theta-to-beta ratio is less than 4 and said P100Max number (measured in microvolts) is greater than or equal to 10.0 microvolts; and identifying the person as having at least one other affective disorder if said theta-to-beta ratio is less than 4 and said P200Max number (measured in microvolts) is greater than or equal to 6.0 microvolts.

20. A method of identifying the low sensory input system attentional disorder(s) of a person, said method for use with an EEG Data Acquisition and Analysis System which is electrically interconnected to a head assembly containing a plurality of EEG electrodes for sensing brain waves, wherein said method further utilizes a device operable to display a series of paradigms of a pre-selected design, illumination, and frequency, said paradigms evoking brain wave responses sensed by said EEG electrodes and sent to a microprocessor for synchronizing the recording and averaging, said method comprising the steps of: attaching said electrodes to the scalp of said person at predetermined electrode placement locations for measuring said person's brain waves, wherein electrode placement is made in accordance with the American Electroencephalographic Society's Electrode Placement International 10–20 Standard System, wherein said Standard System defines locations CZ, O1, O2, F3, and F4, and wherein said first electrode placement location is at CZ, wherein said second electrode placement location is at O1, wherein said third electrode placement location is at O2; wherein said fourth electrode placement location is at F3; and wherein said fifth electrode placement location is at F4; positioning said person to view said paradigms; displaying to said person sequentially displayed paradigms; measuring the maximum amplitude of theta activity at a first electrode placement location during a plurality of points in time after termination of each of the displays of said paradigms, averaging said theta activity measurements to determine a theta number, wherein said maximum amplitude of theta activity is measured immediately after the termination of each of the displays of said paradigms; measuring the maximum amplitude of beta activity at said first electrode placement location during a plurality of points in time after termination of each of the displays of said paradigms, averaging said beta activity measurements to determine a beta number, wherein said maximum amplitude of beta activity is measured immediately after the termination of each of the displays of said paradigms; determining a theta-to-beta ratio by dividing said theta number by said beta number; simultaneously measuring a first maximum positive voltage potential at a second electrode placement location and at a third electrode placement location during a plurality of predetermined points in time after termination of each of the displays of said paradigms, averaging said first maximum positive voltage potential measurements to determine a P100MAX number, wherein the measurement of the first maximum positive voltage potential at the second and third electrode placement locations takes place approximately 100 milliseconds after termination of each of the displays of said paradigms; simultaneously measuring a second maximum positive voltage potential at a fourth electrode placement location and at a fifth electrode placement location during a plurality of predetermined points in time after termination of each of the displays of said paradigms, averaging said second maximum positive voltage potential measurements to determine a P200MAX number, wherein the measurement of the second first maximum positive voltage potential at the fourth and fifth electrode placement locations takes place approximately 200 milliseconds after termination of each of the displays of said paradigms; identifying the person as having a low sensory attentional disorder if said theta-to-beta ratio is greater than or equal to 4; identifying the person as having a some other, attentive type, disorder if said theta-to-beta ratio is less than 4; identifying the person as having a low sensory attentional disorder and at least one other affective disorder if said theta-to-beta ratio is greater than or equal to 4 and said P100Max number (measured in microvolts) is greater than or equal to 10.0 microvolts; identifying the person as having a low sensory attentional disorder and at least one other affective disorder if said theta-to-beta ratio is greater than or equal to 4 and said P200Max number (measured in microvolts) is greater than or equal to 6.0 microvolts; identifying the person as having only one affective disorder if said theta-to-beta ratio is less than 4 and said P100Max number (measured in microvolts) is less than 10.0 microvolts; identifying the person as having only one affective disorder if said theta-to-beta ratio is less than 4 and said P200Max number (measured in microvolts) is less than 6.0 microvolts; identifying the person as having at least one other affective disorder if said theta-to-beta ratio is less than 4 and said P100Max number (measured in microvolts) is greater than or equal to 10.0 microvolts; and, identifying the person as having at least one other affective disorder if said theta-to-beta ratio is less than 4 and said P200Max number (measured in microvolts) is greater than or equal to 6.0 microvolts.

* * * * *